US 8,764,768 B2

(12) United States Patent
Karpiel (10) Patent No.: US 8,764,768 B2
(45) Date of Patent: Jul. 1, 2014

(54) STAPLING DEVICE FOR CLOSING PERFORATIONS

(75) Inventor: John A. Karpiel, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 696 days.

(21) Appl. No.: 12/548,868

(22) Filed: Aug. 27, 2009

(65) Prior Publication Data

US 2010/0057101 A1 Mar. 4, 2010

Related U.S. Application Data

(60) Provisional application No. 61/093,067, filed on Aug. 29, 2008.

(51) Int. Cl.
*A61B 17/10* (2006.01)
*A61B 17/08* (2006.01)

(52) U.S. Cl.
USPC .......................... 606/142; 606/219; 227/175.1

(58) Field of Classification Search
USPC ................... 606/139–143, 151, 157, 75, 219; 227/175.1
See application file for complete search history.

(56) References Cited

U.S. PATENT DOCUMENTS

| | | | |
|---|---|---|---|
| 3,385,299 A * | 5/1968 | Le Roy | 606/218 |
| 3,814,104 A | 6/1974 | Irnich et al. | |
| 3,856,016 A | 12/1974 | Davis | |
| 3,870,048 A | 3/1975 | Yoon | |
| 3,911,923 A | 10/1975 | Yoon | |
| 3,954,108 A | 5/1976 | Davis | |
| 3,958,576 A | 5/1976 | Komiya | |
| 3,967,625 A | 7/1976 | Yoon | |
| 3,989,049 A | 11/1976 | Yoon | |
| 4,085,743 A | 4/1978 | Yoon | |
| 4,103,680 A | 8/1978 | Yoon | |
| 4,204,541 A | 5/1980 | Kapitanov | |

(Continued)

FOREIGN PATENT DOCUMENTS

EP 0310582 A1 4/1989
EP 0774237 A2 5/1997

(Continued)

OTHER PUBLICATIONS

PCT Publication with International Search Report for PCT/US09/55167.

(Continued)

*Primary Examiner* — Julian W Woo
(74) *Attorney, Agent, or Firm* — Brinks Gilson & Lione (57) ABSTRACT

Medical devices and systems for easily and reliably closing a perforation in tissue. One embodiment of a medical device for use with a scope includes a tubular member having a distal end, an exterior surface and an interior space. A carrier element extends along the exterior surface and around the distal end of the tubular member. An elastic band is positioned on the carrier element around the exterior surface of the tubular member. A staple is positioned within the interior space of a tubular member and includes first and second prongs which are spaced apart and translatable relative to one another. The carrier element is structured to deliver the elastic band beyond the distal end of the tubular member where upon the elastic band contracts and engages the staple to translate the first and second prongs towards each other.

20 Claims, 9 Drawing Sheets

(56) References Cited

U.S. PATENT DOCUMENTS

| | | | |
|---|---|---|---|
| 4,217,902 A | 8/1980 | March | |
| 4,374,523 A | 2/1983 | Yoon | |
| 4,448,194 A | 5/1984 | DiGiovanni et al. | |
| 4,485,816 A | 12/1984 | Krumme | |
| 4,749,114 A | 6/1988 | Green | |
| 4,773,420 A | 9/1988 | Green | |
| 4,791,707 A | 12/1988 | Tucker | |
| 4,796,627 A | 1/1989 | Tucker | |
| 4,821,939 A | 4/1989 | Green | |
| 5,015,249 A | 5/1991 | Nakao et al. | |
| 5,049,153 A | 9/1991 | Nakao et al. | |
| 5,084,057 A | 1/1992 | Green et al. | |
| 5,099,827 A | 3/1992 | Melzer et al. | |
| 5,100,420 A | 3/1992 | Green et al. | |
| 5,156,609 A | 10/1992 | Nakao et al. | |
| 5,192,303 A | 3/1993 | Gatturna et al. | |
| 5,318,221 A | 6/1994 | Green et al. | |
| 5,320,630 A | 6/1994 | Ahmed | |
| 5,324,307 A | 6/1994 | Jarrett et al. | |
| 5,334,217 A | 8/1994 | Das | |
| 5,368,599 A | 11/1994 | Hirsch et al. | |
| 5,368,600 A | 11/1994 | Failla et al. | |
| 5,395,381 A | 3/1995 | Green et al. | |
| 5,398,844 A * | 3/1995 | Zaslavsky et al. | 221/208 |
| 5,403,329 A | 4/1995 | Hinchcliffe | |
| 5,403,342 A | 4/1995 | Tovey et al. | |
| 5,405,072 A | 4/1995 | Zlock et al. | |
| 5,411,522 A | 5/1995 | Trott | |
| 5,484,451 A | 1/1996 | Akopov et al. | |
| 5,520,701 A * | 5/1996 | Lerch | 606/142 |
| 5,573,543 A | 11/1996 | Akopov et al. | |
| 5,582,615 A | 12/1996 | Foshee et al. | |
| 5,582,616 A | 12/1996 | Bolduc et al. | |
| 5,593,414 A | 1/1997 | Shipp et al. | |
| 5,667,527 A | 9/1997 | Cook et al. | |
| 5,674,231 A | 10/1997 | Green et al. | |
| 5,779,720 A | 7/1998 | Walder-Utz et al. | |
| 5,868,763 A | 2/1999 | Spence et al. | |
| 5,972,002 A | 10/1999 | Bark et al. | |
| 5,976,159 A | 11/1999 | Bolduc et al. | |
| 5,984,917 A | 11/1999 | Fleischman et al. | |
| 6,113,612 A | 9/2000 | Swanson et al. | |
| 6,149,658 A | 11/2000 | Gardiner et al. | |
| 6,152,937 A | 11/2000 | Peterson et al. | |
| 6,159,223 A | 12/2000 | Danks et al. | |
| 6,171,321 B1 | 1/2001 | Gifford, III et al. | |
| 6,183,486 B1 | 2/2001 | Snow et al. | |
| 6,193,732 B1 | 2/2001 | Frantzen et al. | |
| 6,228,055 B1 | 5/2001 | Foerster et al. | |
| 6,306,150 B1 | 10/2001 | Levinson | |
| 6,402,765 B1 | 6/2002 | Monassevitch et al. | |
| 6,428,548 B1 | 8/2002 | Durgin et al. | |
| 6,446,854 B1 | 9/2002 | Remiszewski et al. | |
| 6,582,452 B2 | 6/2003 | Coleman et al. | |
| 6,623,510 B2 | 9/2003 | Belef et al. | |
| 6,699,256 B1 | 3/2004 | Logan et al. | |
| 6,719,777 B2 | 4/2004 | Ginn et al. | |
| 6,746,460 B2 | 6/2004 | Gannoe et al. | |
| 6,776,783 B1 | 8/2004 | Frantzen et al. | |
| 6,849,078 B2 | 2/2005 | Durgin et al. | |
| 6,884,248 B2 | 4/2005 | Bolduc et al. | |
| 6,911,032 B2 | 6/2005 | Jugenheimer et al. | |
| 6,913,607 B2 | 7/2005 | Ainsworth et al. | |
| 6,926,731 B2 | 8/2005 | Coleman et al. | |
| 6,974,466 B2 | 12/2005 | Ahmed et al. | |
| 7,001,398 B2 | 2/2006 | Carley et al. | |
| 7,018,388 B2 | 3/2006 | Yencho et al. | |
| 7,059,508 B2 | 6/2006 | Shelton, IV et al. | |
| 7,060,021 B1 * | 6/2006 | Wilk | 600/16 |
| 7,060,084 B1 | 6/2006 | Loshakove et al. | |
| 7,112,214 B2 | 9/2006 | Peterson et al. | |
| 7,211,101 B2 | 5/2007 | Carley et al. | |
| RE39,841 E | 9/2007 | Bilotti | |
| 7,331,968 B2 | 2/2008 | Arp et al. | |
| RE40,237 E | 4/2008 | Bilotti et al. | |
| 7,357,287 B2 | 4/2008 | Shelton, IV et al. | |
| 7,364,061 B2 | 4/2008 | Swayze et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,404,509 B2 | 7/2008 | Ortiz et al. | |
| 7,407,074 B2 | 8/2008 | Ortiz et al. | |
| 7,407,077 B2 | 8/2008 | Ortiz et al. | |
| 7,410,086 B2 | 8/2008 | Ortiz et al. | |
| 7,416,101 B2 | 8/2008 | Shelton, IV et al. | |
| D576,278 S | 9/2008 | Nalagatla et al. | |
| 7,419,080 B2 | 9/2008 | Smith et al. | |
| 7,422,139 B2 | 9/2008 | Shelton, IV et al. | |
| 7,451,904 B2 | 11/2008 | Shelton, IV | |
| 7,455,208 B2 | 11/2008 | Wales et al. | |
| 7,608,091 B2 | 10/2009 | Goldfarb et al. | |
| 7,641,652 B2 | 1/2010 | Coe et al. | |
| 7,655,015 B2 | 2/2010 | Goldfarb et al. | |
| 7,666,197 B2 | 2/2010 | Orban, III | |
| 7,722,628 B2 | 5/2010 | Stokes et al. | |
| 7,727,247 B2 | 6/2010 | Kimura et al. | |
| 7,727,248 B2 | 6/2010 | Smith et al. | |
| 7,736,388 B2 | 6/2010 | Goldfarb et al. | |
| 2003/0078598 A1 | 4/2003 | Ginn et al. | |
| 2003/0158578 A1 | 8/2003 | Pantages et al. | |
| 2003/0195561 A1 | 10/2003 | Carley et al. | |
| 2004/0009289 A1 | 1/2004 | Carley et al. | |
| 2004/0039414 A1 | 2/2004 | Carley et al. | |
| 2004/0073236 A1 | 4/2004 | Carley et al. | |
| 2004/0087981 A1 | 5/2004 | Berube et al. | |
| 2004/0097982 A1 | 5/2004 | Jugenheimer et al. | |
| 2004/0249412 A1 | 12/2004 | Snow et al. | |
| 2005/0119695 A1 | 6/2005 | Carley et al. | |
| 2005/0192596 A1 | 9/2005 | Jugenheimer et al. | |
| 2005/0283188 A1 | 12/2005 | Loshakove et al. | |
| 2006/0106405 A1 | 5/2006 | Fann et al. | |
| 2006/0135989 A1 | 6/2006 | Carley et al. | |
| 2006/0167484 A1 | 7/2006 | Carley et al. | |
| 2006/0190038 A1 | 8/2006 | Carley et al. | |
| 2006/0237022 A1 | 10/2006 | Chen et al. | |
| 2006/0237023 A1 | 10/2006 | Cox et al. | |
| 2007/0123840 A1 | 5/2007 | Cox | |
| 2007/0233187 A1 | 10/2007 | Lobello | |
| 2007/0276416 A1 | 11/2007 | Ginn et al. | |
| 2008/0027272 A1 | 1/2008 | Kadykowski | |
| 2008/0086153 A1 | 4/2008 | Sakamoto et al. | |
| 2008/0091059 A1 | 4/2008 | Machold | |
| 2008/0097489 A1 | 4/2008 | Goldfarb et al. | |
| 2008/0114380 A1 | 5/2008 | Takemoto et al. | |
| 2008/0114398 A1 | 5/2008 | Phillips et al. | |
| 2008/0140095 A1 | 6/2008 | Smith et al. | |
| 2008/0147116 A1 | 6/2008 | Smith et al. | |
| 2008/0228199 A1 | 9/2008 | Cropper et al. | |
| 2008/0255423 A1 | 10/2008 | Kondo et al. | |
| 2008/0269566 A1 | 10/2008 | Measamer | |
| 2008/0275297 A1 | 11/2008 | Bakos et al. | |
| 2008/0281354 A1 | 11/2008 | Cropper et al. | |
| 2008/0294178 A1 | 11/2008 | Kortenbach et al. | |
| 2008/0296344 A1 | 12/2008 | Cropper et al. | |
| 2008/0300547 A1 | 12/2008 | Bakos | |
| 2008/0300608 A1 | 12/2008 | Measamer | |
| 2008/0300624 A1 | 12/2008 | Schwemberger et al. | |
| 2009/0018552 A1 | 1/2009 | Lam et al. | |
| 2009/0088797 A1 | 4/2009 | Crombie et al. | |
| 2009/0222029 A1 | 9/2009 | Gordin et al. | |
| 2009/0299385 A1 | 12/2009 | Stefanchik et al. | |
| 2009/0306686 A1 | 12/2009 | Ohdaira | |
| 2009/0312773 A1 | 12/2009 | Cabrera et al. | |
| 2009/0318936 A1 | 12/2009 | Harris et al. | |
| 2010/0010508 A1 | 1/2010 | Takahashi et al. | |
| 2010/0010509 A1 | 1/2010 | Ishioka et al. | |
| 2010/0010511 A1 | 1/2010 | Harris et al. | |
| 2010/0010514 A1 | 1/2010 | Ishioka et al. | |
| 2010/0010520 A1 | 1/2010 | Takahashi et al. | |
| 2010/0121351 A1 | 5/2010 | Whitfield et al. | |

(56) References Cited

U.S. PATENT DOCUMENTS

FOREIGN PATENT DOCUMENTS

| EP | 1437096 | 7/2004 |
|----|---------|--------|
| WO | WO88/01486 | 3/1988 |
| WO | WO95/21575 | 8/1995 |
| WO | WO96/40356 | 12/1996 |
| WO | WO98/18389 | 5/1998 |
| WO | WO99/62408 | 12/1999 |
| WO | WO00/56223 | 9/2000 |
| WO | WO00/56227 | 9/2000 |
| WO | WO01/35832 A3 | 5/2001 |
| WO | WO2007/025019 | 3/2007 |

OTHER PUBLICATIONS

Bhat et al., "Transluminal endosurgery: novel use of endoscopic tacks for the closure of access sites in natural orifice transluminal endoscopic surgery (with videos)." *J Gastrointestinal Endoscopy*, 2009, vol. 69, No. 6, pp. 1161-1166.

Desilets et al., "Loop-anchor purse-string versus endoscopic clips for gastric closure: a natural orifice transluminal endoscopic surgery comparison study using burst pressures." *J Gastrointestinal Endoscopy*, 2009, vol. 70, No. 6, pp. 1225-1230.

Huel et al., "A novel double-endoloop technique for natural orifice transluminal endoscopic surgery gastric access site closure." *J Gastrointestinal Endoscopy*, 2010, vol. 71, No. 4, pp. 806-811.

Rengen et al., "Detachable Snares (Endoloop)." *J Techniques in Gastrointestinal Endoscopy*, 2006, Elsevier, Inc., pp. 12-15.

Romanelli et al., "Natural orifice transluminal endoscopic surgery gastrotomy closure in porcine explants with the Padlock-G clip using the Lock-It-System." *J Endoscopy 2010*, vol. 42, pp. 306-310.

Schurr et al., "An over-the-scope clip (OTSC) system for closure of iatrogenic colon perforations: results of an experimental survival study in pigs." *J Endoscopy 2008*, vol. 40, pp. 584-588.

Sclabas et al., "Endoluminal Methods for Gastrotomy Closure in Natural Orifice TransEnteric Surgery (NOTES)." *J Surgical Innovation*, Mar. 2006, vol. 13, No. 1, pp. 23-30.

Sporn et al., "Endoscopic colostomy closure after full thickness excision: comparison of T fastener with multiclip applier." *J Endoscopy 2008*, vol. 40, pp. 589-594.

Voermans et al., "In vitro comparison and evaluation of seven gastric closure modalities for natural orifice transluminal endoscopic surgery (NOTES)." *J Endoscopy 2008*, vol. 40, pp. 595-601.

\* cited by examiner

STAPLING DEVICE FOR CLOSING PERFORATIONS

CROSS-REFERENCE TO RELATED APPLICATIONS

This application claims the benefit of U.S. Provisional Application Ser. No. 61/093,067 filed on Aug. 29, 2008, entitled "STAPLING DEVICE FOR CLOSING PERFORATIONS" the entire contents of which are incorporated herein by reference.

BACKGROUND OF THE INVENTION

Perforations in the walls of internal organs may be naturally occurring, or formed intentionally or unintentionally. In order to permanently close these perforations and allow the tissue to properly heal, numerous medical devices and methods have been developed employing sutures, adhesives, clips, staples, anchors and the like. Many of these devices typically employ one or more sutures, the strands of which must be brought together and fixed in place in order to close the perforation.

Manually tying sutures strands together to close a perforation can be very complex and time consuming. For example, a significant level of skill and coordination is required by the medical professional, especially when the perforation and sutures are difficult to access within the body, such as in endoscopic or laparoscopic procedures. The numerous difficulties with manually tying sutures are well documented. In order to address these and other issues of manual suture tying, various automatic suture tying systems have been developed. Unfortunately, such automatic systems are often complex and costly, difficult to use, and limited in the variety of situations where they may be employed.

BRIEF SUMMARY OF THE INVENTION

The present invention provides medical devices and systems for easily and reliably closing a perforation in tissue. One embodiment of a medical device, constructed in accordance with the teachings of the present invention, includes a tubular member having a distal end, an exterior surface and an interior space. A carrier element extends along the exterior surface and around the distal end of the tubular member. An elastic band is positioned on the carrier element around the exterior surface of the tubular member. A staple is positioned within the interior space of a tubular member and includes first and second prongs which are spaced apart and translatable relative to one another. The carrier element is structured to deliver the elastic band beyond the distal end of the tubular member where upon the elastic band contracts and engages the staple to translate the first and second prongs towards each other.

According to more detailed aspects of this embodiment, the tubular member may define a slot extending proximally from the distal end, and a portion of the staple extends through the slot. The elastic band engages the portion of the staple extending through the slot, whereby distal translation of the elastic band causes distal translation of the staple. Similarly, the tubular member may define first and second slots, and first and second portions of the staple extend through the slots and engage the elastic band for distal translation. The first prong of the staple may be linearly translatable relative to the second prong, or may be pivotable relative to the second prong.

According to another embodiment constructed in accordance with the teachings of the present invention, a surgical staple is provided for closing a perforation in tissue. The staple generally includes a first prong having a first connector, a second prong having a second connector. The first connector is adjustable relative to the second connector such that the first prong is translatable relative to the second prong. According to more detailed aspects of this embodiment, each of the first and second prongs includes a first end defining a piercing tip. Translation of the first prong relative to the second prong draws the piercing tips into close proximity. The first ends of the first and second prongs are curved, and preferably the first and second prongs are oriented such that the first ends curve towards each other. Each of the first and second prongs includes a second end opposite the first end, each of the second ends extending outwardly to define a retaining tip. The first connecting member is typically one of a rod in a first tube, and the second connection member is typically one of a passageway formed in the second prong or a second tube sized to receive the first connecting member. Alternatively, the first and second connection members are hinged portions pivotally connecting the first and second prongs. The first and second prongs may be biased away from each other.

In another embodiment constructed in accordance with the teachings of the present invention, a medical system is provided for closing a perforation in tissue. The medical system generally includes an endoscope having a channel and a tubular member fitted to the endoscope. A carrier element extends along the exterior surface and around the distal end of the tubular member, and an elastic band is positioned on the carrier element around the exterior surface of the tubular member. A staple is positioned within the interior space of the tubular member and includes a first prong spaced apart from a second prong and translatable relative thereto. An actuator extends through the channel of the endoscope and is connected to the carrier element. Proximal retraction of the actuator delivers the elastic band beyond the distal end of the tubular member, whereupon the elastic band contracts. The elastic band engages the staple when it contracts to translate the first and second prongs towards each other.

According to more detailed aspects of this embodiment, the medical system may further include an advancing member extending to a channel of the endoscope and position to engage the staple. Distal translation of the advancing member causes distal translation of the staple. The advancing member may be operably connected to the actuator such that distal translation of the advancing member is coordinated with proximal translation of the actuator. The medical system may include one staple, and more preferably includes a plurality of staples arranged in series within the tubular member and a plurality of elastic bands positioned on the carrier element. The plurality of staples are preferably oriented such that their piercing tips face distally for engaging the tissue.

DETAILED DESCRIPTION OF THE INVENTION

In the present application, the terms "proximal" and "proximally" refer to a position, direction, or orientation that is generally towards a physician during a medical procedure, while the terms "distal" and "distally" refer to a position, direction, or orientation that is generally away from the physician and towards a target site within a patient's anatomy during a medical procedure. Thus, "proximal" and "distal" portions of a device or bodily region may depend on the point of entry for the procedure (e.g., percutaneously or laparoscopically or endoscopically).

Figure 1:
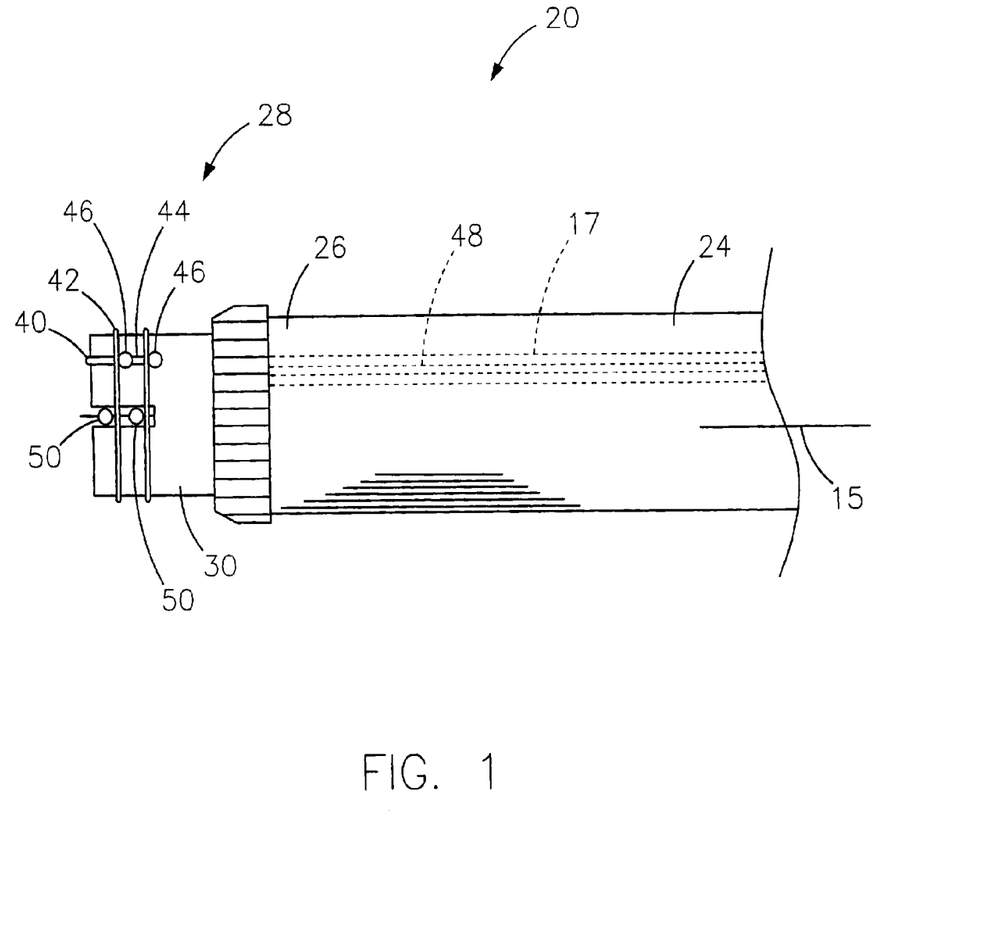
FIG. 1 is a plan view of a medical system constructed in accordance with the teachings of the present invention.
Figure 2:
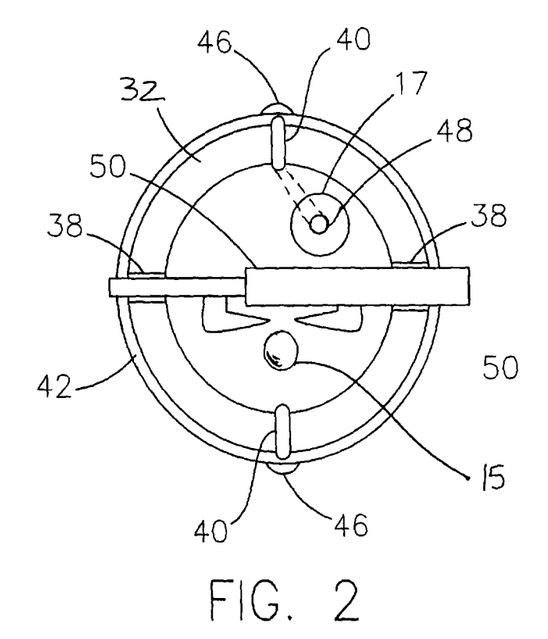
FIG. 2 is an end view of the medical system depicted in FIG. 1.
Figure 3:
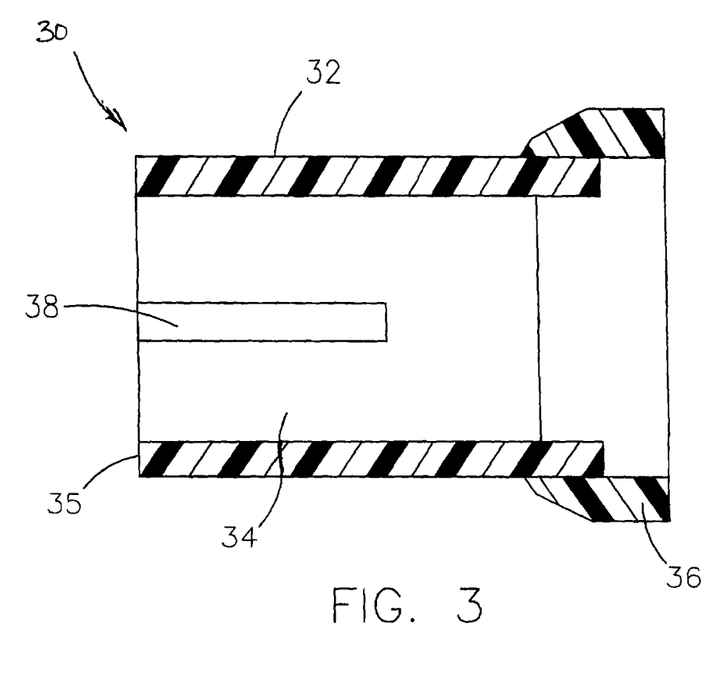
FIG. 3 is a cross-sectional view of an end cap forming a portion of the medical system depicted in FIG. 1.

Turning now to the figures, FIG. 1 is a plan view of a medical system 20 for closing a perforation 14 in tissue 12 (see FIG. 4) constructed in accordance with the teachings of the present invention. The medical system 20 generally comprises an endoscope 24 having a distal end 26 and a medical device 28 attached to the distal end 26 of the endoscope 24. The medical device 28 includes an end cap 30, best seen in the cross-sectional view of FIG. 3, and can be adapted for a variety of different types of scopes. The end cap 30 generally includes a tubular member 32 defining an interior space 34, and a collar 36 affixed to the tubular member 32 and sized to receive the endoscope 24 therein. It will be recognized that the end cap 30, and in particular the tubular member 32, may be connected to the endoscope 24 in various manners including differently structured collars 36, friction fits, adhesives and other mechanical attachment mechanisms. Likewise, the tubular member 32 may have various constructions, including members that are somewhat solid, so long as the member defines an interior space 34 sized to receive a staple as further described hereinbelow. The tubular member 32 generally includes a distal end 35 and at least one slot 38. As best seen in FIGS. 1 and 2, the tubular member 32 defines two slots 38 which are circumferentially spaced apart by about 180 degrees, and extend proximally from the distal end 35 of the tubular member 32.

The medical device 28 further includes a carrier element 40 extending along the exterior surface of the tubular member 32 and around the distal end 35 of the tubular member 32. One or more elastic bands 42 are positioned on the carrier element 40 and around the exterior surface of the tubular member 32. The carrier element 40 has been depicted as a strand 44 comprising a thread or suture having a gripping member 46 formed thereon, such as knot in the suture. It will be recognized that numerous different types of carrier elements 40 may be employed, such as other strings, tethers, fabrics, strips of material, or tubular members which are sized to receive and distally translate a plurality of bands 42. See, for example, U.S. Pat. Nos. 5,320,630 and 6,974,466, the disclosures of which are incorporated herein by reference in their entirety.

Figure 4:
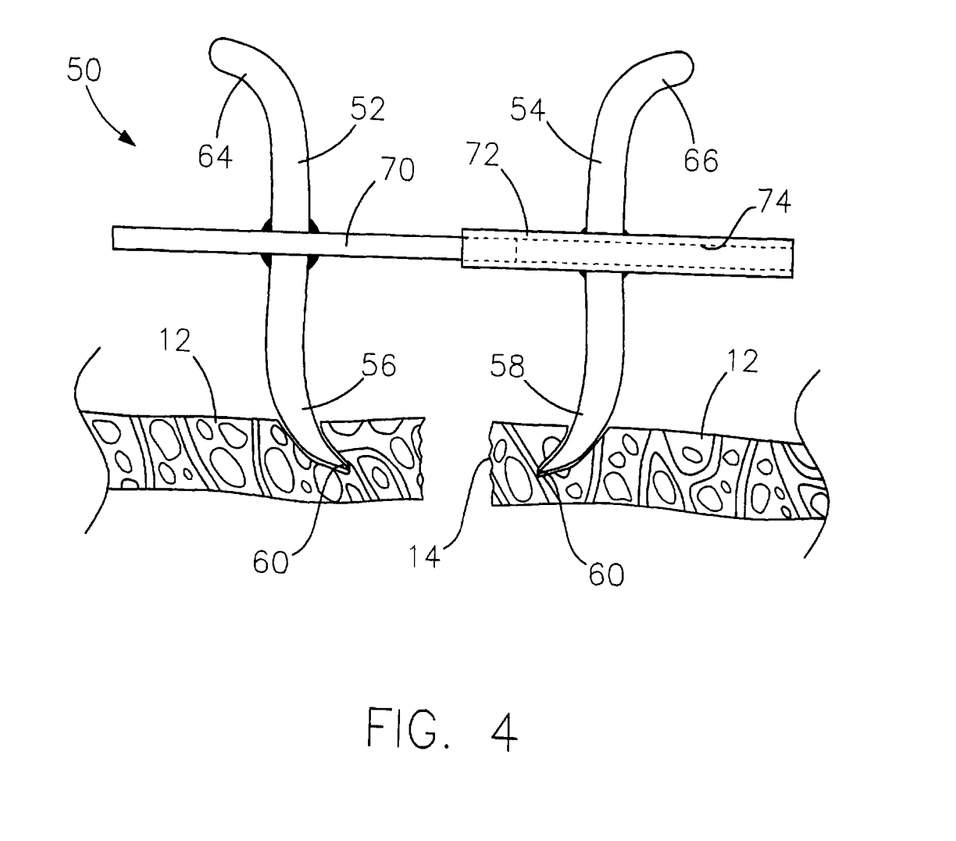
FIG. 4 is a side view of a surgical staple constructed in accordance with the teachings of the present invention.

One or more staples 50 are positioned within the interior space 34 of the tubular member 32. As best seen in FIG. 4, each staple 50 includes a first prong 52 and a second prong 54 which are spaced apart and translatable relative to one another. The first and second prongs 52, 54 include first ends 56, 58 and opposing second ends 64, 66, respectively. The first ends 56, 58 define piercing tips 60, which are shown are curved and oriented to point towards the opposing prong 54, 52.

Disclosed herein are several ways to provide adjustability to the staple 50 such that the first and second prongs 52, 54 are translatable relative to one another. In the embodiment depicted in FIG. 4, the first prong 52 includes a first connection member 70 while the second prong 54 includes a second connection member 72. The first connection member 70 is a rod or tube that is slidably received by the second connection member 72. The second connection member 72 has been depicted in the form of a tube defining an interior lumen 74. The connection members 70, 72 may be attached to the first and second prongs 52, 54 in many different manners, such as by mechanical fastening, welding, bonding, adhesives, integral formation (e.g. molding or casting) or the like.

As best seen in FIG. 1, the piercing tip 60 of the first and second prongs 52, 54 are oriented within the end cap 30 to face distally for piercing the tissue 12, as shown in FIG. 4. As best seen in FIG. 2, each staple extends through the slots 38 in the tubular member 32, and more particularly the first and second connection members 70, 72 each extend through one slot 38. As such, the first and second connection members 70, 72 may be engaged by the bands 42 positioned around the exterior of the end cap 30 and on the carrier element 40.

The endoscope 24 typically includes an accessory channel 17, and the medical device 28 further includes an actuator extending through the channel 17 and connected to the carrier element 40. Proximal retraction of the actuator 48 causes the carrier element 40 to move distally over the exterior surface of the tubular member 32, which in turn delivers the elastic bands 42 beyond the distal end 35 of the tubular member 32 and end cap 30. Similarly, because each staple 50 includes portions extending through slots 38 and engaging the elastic bands 42, the staples 50 are also moved distally beyond the distal end 35 of the tubular member 32. Upon being freed from the end cap 30, the elastic band 42 contracts, and in particular engages the staple to translate the first and second prongs 52, 54 towards each other. The second ends 64, 66 of the first and second prongs 52, 54 may be curved, bent or otherwise extend outwardly to define a retaining tip which is sized to receive and retain the elastic band 40 on the staple 50.

Figure 5:
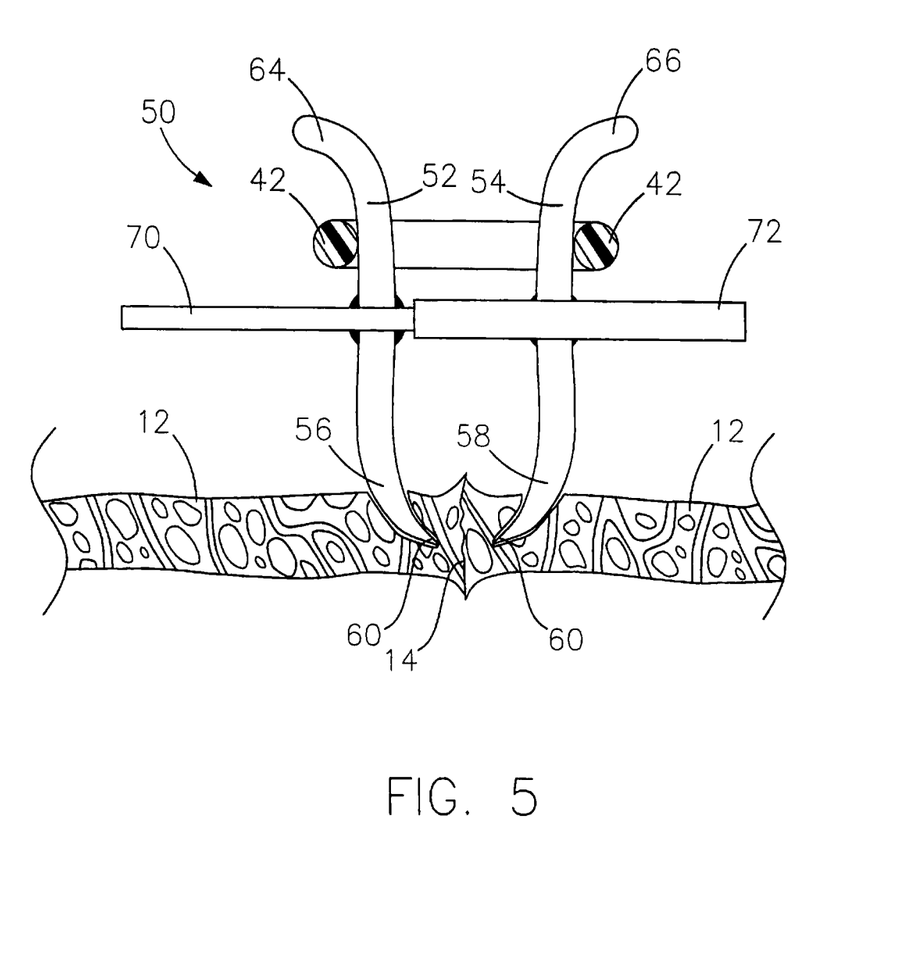
FIG. 5 is a side view similar to FIG. 4 showing deployment of the surgical staple by the medical system depicted in FIG. 1.
Figure 6:
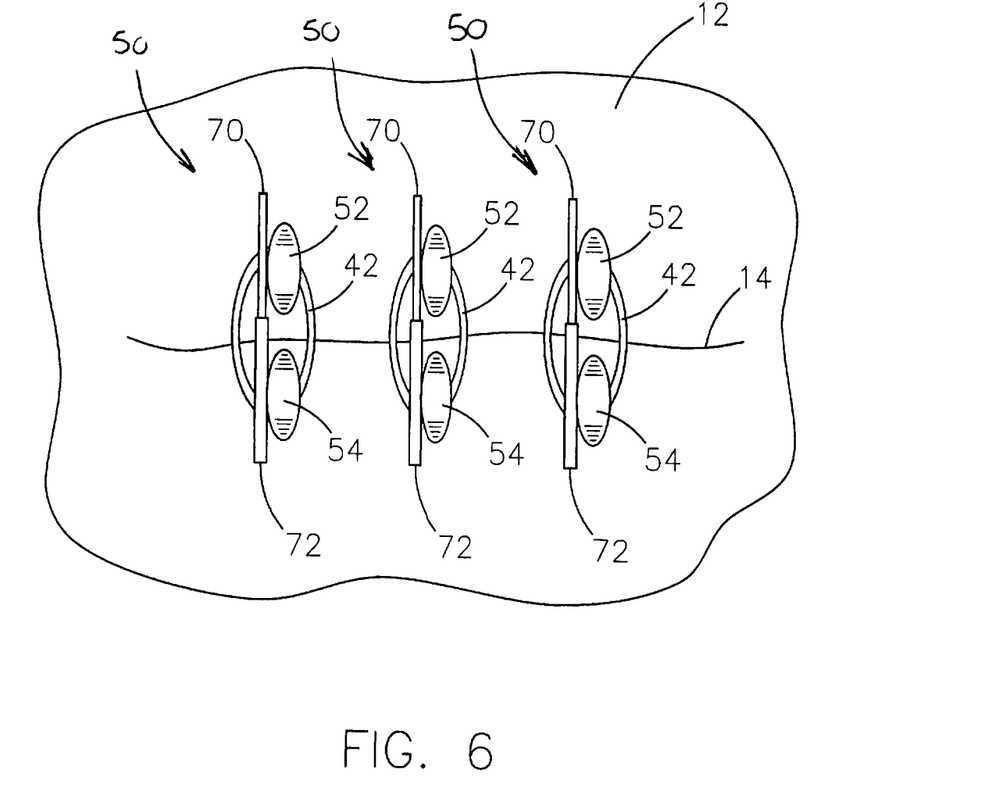
FIG. 6 is plan view showing deployment of a plurality of surgical staples to cause a perforation in tissue.

Deployment of the medical system 20 and medical device 28 generally includes delivering the endoscope 24 (having the medical device 28 attached thereto) through the bodily lumen of a patient to a desired location adjacent a perforation 14 formed in tissue 12. As shown in FIG. 4, the medical system 20 may be advanced such that the piercing tips 60 of the leading staple 50 engage the tissue 12 on opposite sides of the perforation 14. The endoscope 24 will typically include a visualization device 15 (FIG. 2) which can assist in placement of each staple 50. Then, the actuator 48 may be proximally retracted to pull the carrier element 40 around the distal end 35 of the tubular member 32, and likewise carry with it an elastic band 42. Distal movement of the elastic band 42 will cause distal movement of the staple 50, embedding or further embedding the prongs 52, 54 of the staple 50 into the tissue 12. Once the elastic band 42 has passed beyond the distal end 35 of the tubular member 32, its natural elasticity causes it to contract. Based on the relative positioning of the elastic band 42 and the prongs 52, 54 of the staple 50, contraction of the elastic band 42 causes the first and second prongs 52, 54 to be drawn closer together as shown in FIG. 5. As depicted, the second connection member 72 slidably received the first connection member 70, such that the first and second prongs 52, 54 linear translate relative to one another and draw the perforation 14 closed. As shown in the top view of FIG. 6, a plurality of staples 50 may be deployed along a perforation 14 to close the perforation 14 along its entire length. In this manner, the perforation in tissue may be reliably closed without the need for sutures or other devices.

Figure 7:
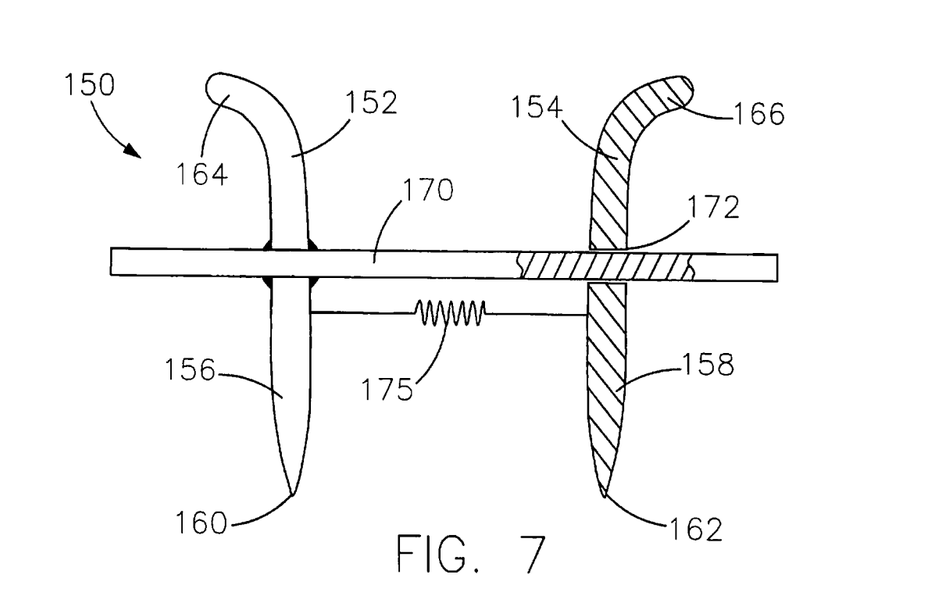
FIG. 7 is a side view, partially in cross section, of an alternate embodiment of a surgical staple constructed in accordance with the teachings of the present invention.

Many variations of the medical system 20 and medical device 28 will be apparent to those skilled in the art. One alternate embodiment of a surgical staple 150 is shown in FIG. 7. In this embodiment, the staple 150 again includes a first prong 152 and a second prong 154 defining first ends 156, 158 having piercing tips 160, 162. In this embodiment, it will be seen that the piercing tips 160, 162 are not curved to face towards each other, but generally face parallel to one another, and when loaded in the end cap 30 are distally facing. The second ends 164, 166 of the first and second prongs 152, 154 again flare outwardly to retain the elastic band thereon. It can also been seen in this embodiment the first connection member 170 is a rod connected to the first prong 152, while the second connection 172 is a passageway formed in the second prong 154. The passageway 172 is sized to slidably receive the rod 170 of the first prong 152. Finally, it will also be noted that spring 175 may be provided between the first and second prongs 152, 154 to bias the two elements apart, thereby promoting placement of each piercing tip 160, 162 on opposing sides of a perforation 14.

Figure 8:
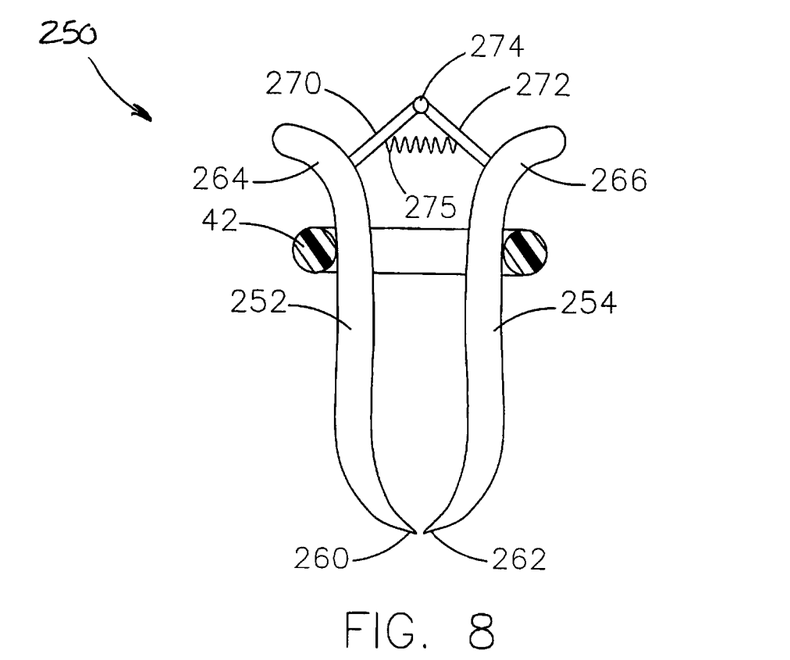
FIG. 8 is a side view of another alternate embodiment of a surgical staple constructed in accordance with the teachings of the present invention.

Yet another embodiment of a surgical staple 250 has been depicted in FIG. 8. In this embodiment, the first prong 252 and second prong 254 have a shape similar to the embodiment of FIGS. 1-6, including first ends 252, 254 defining piercing tips 260, 264 and opposing second ends 264, 266. In this embodiment, the first connection member 270 and second connection member 272 are hinged portions which are pivotally connected about a pivot 274. As such, the first prong 252 and second 254 are pivotable relative to one another to open and close the space between the piercing tips 260, 262. Similar to the embodiment of FIG. 7, a spring 275 or other biasing element may be located between the first and second prongs 252, 254 (or located between the first and second connection member 270, 272) to bias the prongs 252, 254 away from one another. A scissor like pivot may also be used.

Figure 9:
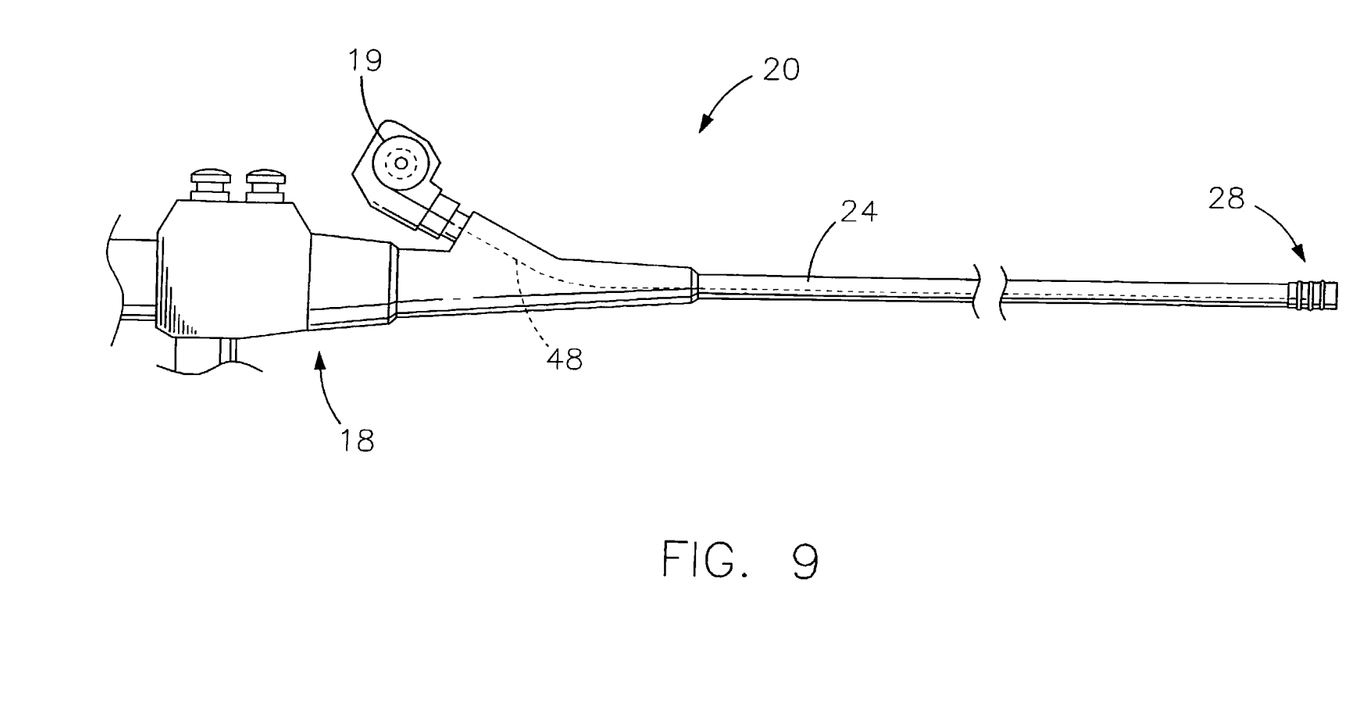
FIG. 9 is a side view of the medical system depicted in FIG. 1.
Figure 10:
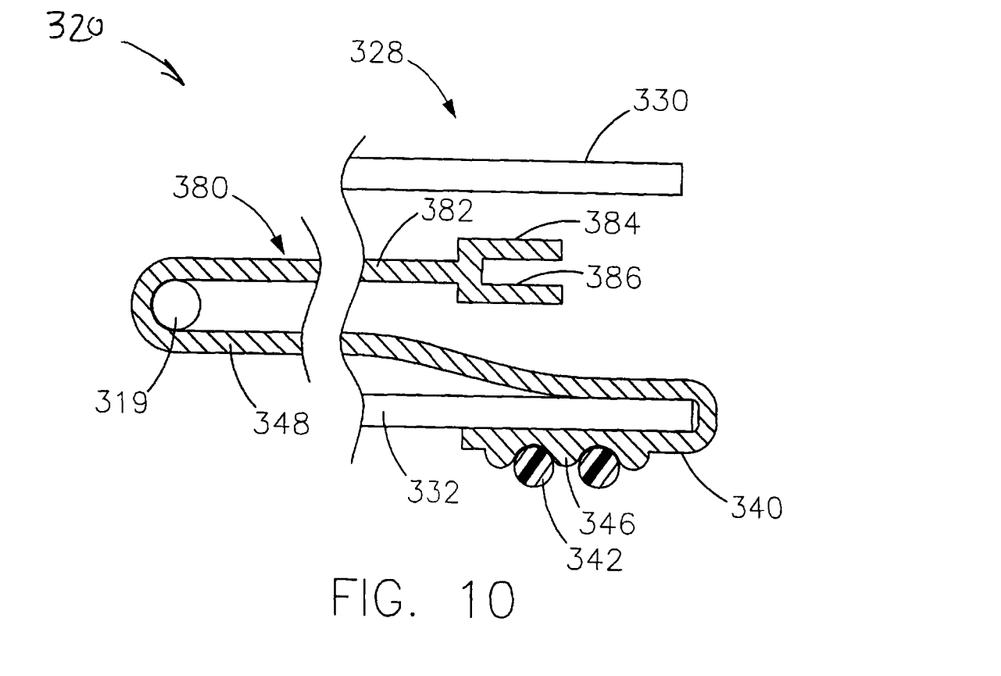
FIG. 10 is an end view of an alternate embodiment of the medical system depicted in FIG. 1.
Figure 11:
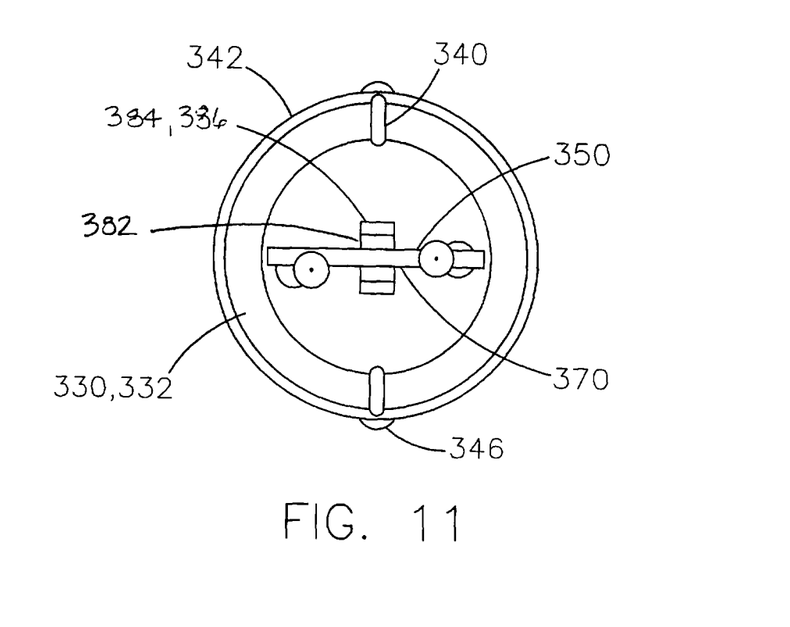
FIG. 11 is a cross-sectional view of the medical system depicted in FIG. 10.

As shown in FIGS. 9-11, the medical system 20 is also subject to several variations. In FIG. 9, the endoscope 24 is shown having a handle assembly 18 and a port for the accessory channel 17. In particular, the actuator 48 extends through the accessory channel 17 and a control knob 19 is connected to the actuator 48 for winding it up on a spool connected to the knob 19 (or the knob 19 forms a spool). In a related embodiment shown in FIGS. 10 and 11, a medical system 320 and medical device 328 include all of the elements of previously discussed embodiments, including an end cap 330 and a carrier element 340 positioned along the exterior surface of tube 332. The carrier element receives a plurality of elastic bands 342 positioned within recesses formed between engaging elements 346 of the carrier element 340. In this embodiment, the medical system 320 further includes an advancing member 380 having a pusher 382 with a forked distal end defined by tines 384, 386 which are structured to extend around a staple 350 and in particular the connector 370 of the staple 350. In this embodiment, the advancing member 380 and actuating member 348 are connected together such that proximal retraction of the actuating member 348 causes distal advancement of the advancing member 380. As shown in FIG. 10, these elements may be connected through the control 319 such that operation of the control knob 319 coordinates the movement of the carrier element 340 and elastic bands 342 relative to the advancing member 380 in the staple 350.

Figure 12:
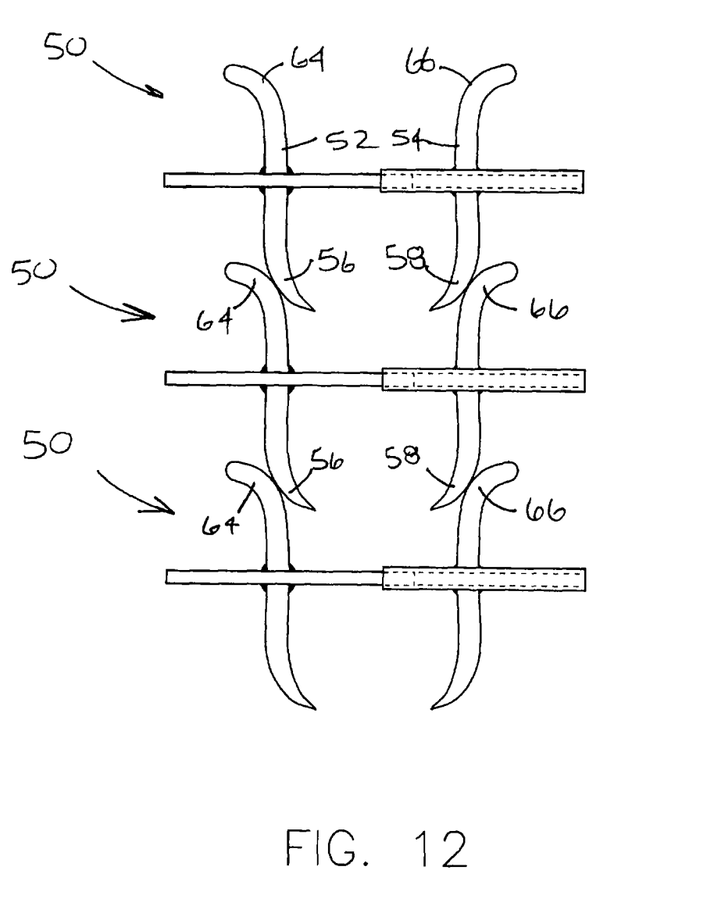
FIG. 12 is a top view of a series of surgical staples forming a part of the medical system depicted in FIGS. 10 and 11.

Finally, and as shown in FIG. 12, a series of staples 50 may be placed in series such that the first ends 56, 58 of the prongs 52, 54 abut against the second ends 64, 66 of the adjacent staple 50. In this manner, a single advancing member, such as the advancing member 380 shown in FIGS. 10 and 11, may be used to press upon one end of the series of staples 50 to translate the entire series of staples 50 distally for placement in the tissue 12 enclosure of the perforation 14.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for closing a perforation in tissue, the medical device comprising:
   a tubular member defining a longitudinal axis and having a distal end, an exterior surface and an interior space, the tubular member defining at least one slot extending laterally through the tubular member and extending proximally from the distal end, the slot opening laterally to communicate the interior space with the exterior surface;
   a carrier element extending along the exterior;
   an elastic band positioned around the exterior surface of the tubular member and engaged with the carrier element;
   a staple positioned within the interior space of the tubular member and translatable beyond the distal end of the tubular member, a portion of the staple extending through the slot, the staple including a first prong spaced apart from a second prong, the first prong translatable relative to the second prong, the first and second prongs each including a first end defining a piercing tip structured to pierce tissue; and
   the carrier element structured to deliver the elastic band beyond the distal end of the tubular member whereupon the elastic band contracts, the elastic band engaging the staple when it contracts to translate the first and second prongs towards each other.

2. The medical device of claim 1, wherein the elastic band engages the portion of the staple extending through the slot, whereby distal translation of the elastic band causes distal translation of the staple.

3. The medical device of claim 1, wherein the tubular member defines first and second slots extending proximally from the distal end, a first portion of the staple extending through the first slot and a second portion of the staple extending through the second slot, and wherein the elastic band engages the first and second portions of the staple.

4. The medical device of claim 1, further comprising an advancing member extending through the tubular member and positioned to engage and distally translate the staple.

5. The medical device of claim 1, wherein the first prong is linearly translatable relative to the second prong.

6. The medical device of claim 1, wherein the first prong is pivotable relative to the second prong.

7. The medical device of claim 1, wherein the staple further includes a first connector connecting member attached to the first prong and a second connecting member attached to the second prong, and wherein the first connecting member is adjustable relative to the second connecting member to adjust the distance between the first and second prongs.

8. The medical device of claim 7, wherein the first connecting member is a rod and the second connecting member is a passageway formed in the second prong.

9. The medical device of claim 7, wherein the first connecting member is one of a rod and a first tube, and wherein the second connection member is a second tube sized to receive the first connecting member.

10. The medical device of claim 7, wherein the first and second connecting members are hinge portions pivotally connecting the first and second prongs.

11. The medical device of claim 7, wherein the first connecting member is the portion of the staple extending through the slot.

12. The medical device of claim 7, wherein the first connecting member slidably receives the second connector.

13. The medical device of claim 7, wherein the first connecting member projects laterally outwardly from the first prong in a direction away from the second prong.

14. The medical device of claim 13, wherein the second connecting member projects laterally outwardly from the second prong in a direction away from the first prong.

15. The medical device of claim 1, wherein the first ends of the first and second prongs are curved, and wherein the first and second prongs are oriented such that the first ends curve towards each other.

16. The medical device of claim 1, wherein each of the first and second prongs include a second end opposite the first end, and wherein each of the second ends laterally project away from the longitudinal axis to define a retaining tip.

17. The medical device of claim 1, wherein the first and second prongs are biased away from each other.

18. The medical device of claim 1, wherein the portion of the staple extending through the slot is positioned along the exterior surface at a location spaced proximally away from the distal end of the tubular member.

19. The medical device of claim 1, wherein the elastic band is positioned on the carrier element.

20. The medical device of claim 1, wherein the carrier element extends around the distal end of the tubular member and into the interior space.

* * * * *